(12) United States Patent
Voth

(10) Patent No.: US 8,535,037 B2
(45) Date of Patent: Sep. 17, 2013

(54) BLOW MOLDING MACHINE WITH CIP SYSTEM FOR PRODUCING PLASTIC BOTTLES, PARTICULARLY PET BOTTLES

(75) Inventor: Klaus Voth, Obertraubling-piesenkofen (DE)

(73) Assignee: Krones AG, Neutraubling (DE)

( * ) Notice: Subject to any disclaimer, the term of this patent is extended or adjusted under 35 U.S.C. 154(b) by 240 days.

(21) Appl. No.: 12/788,341

(22) Filed: May 27, 2010

(65) Prior Publication Data

US 2010/0303946 A1 Dec. 2, 2010

(30) Foreign Application Priority Data

May 29, 2009 (DE) .......................... 10 2009 023 406

(51) Int. Cl.
*B29C 33/72* (2006.01)
*B29C 49/58* (2006.01)

(52) U.S. Cl.
USPC ........... 425/226; 425/225; 425/227; 425/229; 425/535; 425/538

(58) Field of Classification Search
CPC ........ B29C 33/72; B29C 33/722; B29C 49/28
USPC ................. 425/523, 528, 529, 535, 536, 538, 425/225, 226, 227, 229; 264/39; 134/10, 134/22.1
See application file for complete search history.

(56) References Cited

U.S. PATENT DOCUMENTS

| | | | |
|---|---|---|---|
| 3,340,569 A * | 9/1967 | Hagen ............................ | 425/532 |
| 3,650,656 A * | 3/1972 | Schmid .......................... | 425/526 |
| 3,792,144 A * | 2/1974 | Burkett et al. ................. | 264/525 |
| 3,819,317 A * | 6/1974 | Higginbotham ............... | 425/526 |
| 3,924,998 A * | 12/1975 | Moore ........................... | 425/526 |
| 3,993,427 A * | 11/1976 | Kauffman et al. ............ | 425/529 |
| 4,019,849 A * | 4/1977 | Farrell .......................... | 425/445 |
| 4,173,447 A * | 11/1979 | Bradbury ...................... | 425/526 |
| 4,214,860 A | 7/1980 | Kleimenhagen et al. | |
| 4,394,333 A * | 7/1983 | Fukushima et al. ........ | 264/37.15 |
| 4,451,633 A * | 5/1984 | Brownscombe et al. .. | 526/348.6 |
| 5,182,122 A * | 1/1993 | Uehara et al. ................. | 425/526 |

(Continued)

FOREIGN PATENT DOCUMENTS

DE 19713874 A1 10/1998
DE 20018500 U1 12/2001

(Continued)

OTHER PUBLICATIONS

Search Report for DE 10 2009 023 406.3 dated Oct. 5, 2011.

(Continued)

*Primary Examiner* — Seyed Masoud Malekzadeh
(74) *Attorney, Agent, or Firm* — Marshall, Gerstein & Borun LLP

(57) ABSTRACT

A blow molding machine for producing plastic bottles, particularly PET bottles, including a plurality of blow molding stations, which have assigned thereto valve blocks with control valves and blowing nozzles for introducing or discharging blowing air; and a cleaning-in-place (CIP) system for cleaning the blow molding machine. Since the valve blocks are configured such that they can be included in the CIP process, the system components, such as the blowing nozzle, which are particularly important for the production of PET bottles in terms of hygiene, can be cleaned and sterilized without disassembly.

8 Claims, 2 Drawing Sheets

(56) References Cited

U.S. PATENT DOCUMENTS

| | | | |
|---|---|---|---|
| 5,229,043 A * | 7/1993 | Lee | 264/37.16 |
| 5,368,458 A * | 11/1994 | Addeo et al. | 425/4 R |
| 5,622,735 A * | 4/1997 | Krishnakumar et al. | 425/530 |
| 5,962,039 A * | 10/1999 | Katou et al. | 425/210 |
| 6,214,282 B1 * | 4/2001 | Katou et al. | 264/524 |
| 6,423,253 B1 * | 7/2002 | Bunel et al. | 264/37.16 |
| 6,425,751 B1 * | 7/2002 | Bergeron et al. | 425/226 |
| 6,488,491 B1 * | 12/2002 | Nelson et al. | 425/228 |
| 6,585,001 B2 * | 7/2003 | Gatti | 137/533.27 |
| 6,767,197 B2 * | 7/2004 | Boyd et al. | 425/143 |
| 6,849,126 B2 * | 2/2005 | Moore et al. | 118/254 |
| 6,905,326 B2 * | 6/2005 | Voth et al. | 425/529 |
| 7,011,513 B2 * | 3/2006 | Russell | 425/225 |
| 7,247,210 B2 * | 7/2007 | Staub et al. | 134/36 |
| 7,597,732 B2 * | 10/2009 | Yokota et al. | 55/406 |
| 7,699,599 B2 | 4/2010 | Danel et al. | |
| 7,758,333 B2 * | 7/2010 | Halbo et al. | 425/535 |
| 7,892,476 B2 * | 2/2011 | Woods et al. | 264/523 |
| 2002/0076462 A1 * | 6/2002 | Boyd et al. | 425/143 |
| 2003/0094185 A1 * | 5/2003 | Osada et al. | 134/1 |
| 2006/0204608 A1 * | 9/2006 | Neter et al. | 425/547 |
| 2008/0230949 A1 * | 9/2008 | Razgunas et al. | 264/255 |
| 2010/0056707 A1 * | 3/2010 | Hottovy et al. | 524/570 |

FOREIGN PATENT DOCUMENTS

| | | | |
|---|---|---|---|
| DE | 20023423 | | 3/2004 |
| DE | 20023432 U1 | | 4/2004 |
| FR | 2872081 B1 | | 10/2006 |
| WO | WO 02/051620 | * | 7/2002 |
| WO | WO-02092324 A1 | | 11/2002 |
| WO | WO-2007020354 A3 | | 11/2007 |

OTHER PUBLICATIONS

Office Action for Japanese Application No. P2010-119439 dated Jun. 14, 2011.

SIDEL—SRU 10 / SRU 12 / SRU 14 Series2—Manuel de Presentation (Revision 07), Jun. 15, 2004.

Sidel—Annexe 1A and Annexe 1B to Sidel Jun. 15, 2004 Manuel de Presentation (Rev. 7).

Sidel SRU 10 / SRU 12 / SRU 14 Series2 Manual Operateur (Revision 07) Jun. 15, 2004.

Sidel SRU 10 / SRU 12 / SRU 14 Series2 Manuel Technicien & Superviseur (Revision 07) Jun. 15, 2004.

Sidel SRU 10 / SRU 12 / SRU 14 Series2 Manuel Maintenance Fonctionnement Systemes (Revision 07) Jun. 15, 2004.

* cited by examiner

BLOW MOLDING MACHINE WITH CIP SYSTEM FOR PRODUCING PLASTIC BOTTLES, PARTICULARLY PET BOTTLES

CROSS-REFERENCE TO RELATED APPLICATION

The present application claims the benefit of priority of German Application No. 102009023406.3, filed May 29, 2009. The entire text of the priority application is incorporated herein by reference in its entirety.

FIELD OF THE DISCLOSURE

The present disclosure refers to a blow molding machine for producing plastic bottles, particularly PET bottles, and to a method for the cleaning in place of a blow molding machine.

BACKGROUND

The so-called "cleaning in place", also called CIP, is a known method for sterilizing production plants in the food industry, wherein a disassembly of the areas contacted by the product or the intermediate products and auxiliary means can substantially be dispensed with. So far the CIP sterilization of blow molding machines for beverage bottles, as in DE 200 18 500 U1, has however not been possible because the cleaning agents which are normally used for sterilization, e.g. hydrogen peroxide or peracetic acid, attack the pneumatic units of such blow molding machines.

The cleaning and sterilization needed instead of this with partial disassembly of the blow molding machine is time-consuming and responsible for an undesired long standstill time of the machine.

SUMMARY OF THE DISCLOSURE

It is therefore an aspect of the present disclosure to provide a blow molding machine which can be sterilized more easily and faster. A method for cleaning the same is also needed.

This aspect is achieved in that the valve blocks of the blow molding machine are configured such that they can be included in the CIP process.

It is thereby possible to clean and sterilize the system components, such as the blowing nozzle, which are particularly critical in terms of hygiene for the production of PET bottles, substantially without any disassembly.

Preferably, the valves must be operated pneumatically. The blow molding machine can thus be controlled in a reliable and inexpensive way.

In a particularly advantageous development of the invention, CIP shut-off valves for shutting off pneumatic control lines of the control valves are provided on the valves. It can thereby be prevented that aggressive CIP agents can pass through the control line to further control valves and/or into a compressed air network.

Preferably, the valves comprise seals that are resistant to sterilizing CIP agents, particularly to hydrogen peroxide, peracetic acid, alcohol and soap suds. This enables an uncomplicated repeatable cleaning of the valves.

Control valves are conventionally also called pilot valves.

In a particularly advantageous embodiment, the CIP system comprises: a processing unit for circulating and processing a CIP agent; a CIP feed line for the cleaning agent that can be connected to a blowing-air feed line for the control valves; and removable CIP sealing caps for collecting the cleaning agent at the blow molding stations, with the CIP sealing caps being connected to a CIP return line for returning the cleaning agent into the processing unit. As a result, the cleaning agent can be collected entirely and run in a circuit.

Preferably, the blow molding machine further comprises a media distributor for distributing the blowing air over the blow molding stations and for collecting the cleaning agent and for introducing the collected cleaning agent into the CIP return line. As a consequence, the blowing air and the cleaning agent can be distributed in a space-saving way and the blow molding machine can be rapidly changed over from production operation to CIP, and vice versa.

Preferably, a CIP main shut-off valve is provided in the CIP feed line. This valve prevents blowing air from penetrating into the processing unit in the production process and/or cleaning agent from penetrating into the blowing-air stream.

Preferably, a shut-off valve for the blowing air is provided in the blowing-air feed line. Said valve prevents cleaning agent from penetrating into a blowing-air compressor during CIP and/or blowing air from exiting into the CIP circuit.

The problem is also solved with a method for the CIP of the blow molding machine according to the invention, wherein in a step a) a CIP agent is passed through the valve blocks of the blow molding stations, including the valves and the blowing nozzles. System components of the blow molding machine, e.g. the blowing nozzle, which are particularly critical in terms of hygiene for the production of PET bottles, can thus be cleaned and sterilized without disassembly.

Preferably, the CIP method further comprises the following step b): shutting off pneumatic control lines of the control valves, wherein step b) is carried out before step a). Aggressive CIP agents can thus not pass through the control line to further control valves and/or into a compressed air network.

In a particularly advantageous design, the CIP cleaning method further comprises the following step c): connecting a CIP feed line for the cleaning agent with at least one blowing-air feed line to the valves, wherein step c) is carried out before step a). The existing blowing-air channels can thus be cleaned and used for introducing the cleaning agent into the blowing nozzle.

Preferably, the method comprises the following step d): shutting off a section of the blowing-air feed line at the compressor side, wherein step d) is carried out before step a). In the CIP process this prevents cleaning agents from penetrating into a blowing-air compressor and/or blowing air from exiting into the CIP circuit.

Preferably, the method further comprises the following step: collecting the cleaning agent passed through the valve blocks and returning the cleaning agent into a CIP circuit. This prevents the uncontrolled exit of cleaning agent or its dissipation, respectively.

A particularly advantageous configuration of the method comprises the following step: processing the returned cleaning agent and feeding the processed cleaning agent into the CIP circuit. The cleaning agent can thus be used repeatedly with the same cleaning quality. This saves costs and is environmentally friendly.

Preferably, a sterilizing cleaning agent is passed through the valve blocks, particularly hydrogen peroxide, peracetic acid, alcohol and soap suds. The sterilizing process can thus be carried out in the well-established way for beverage systems, particularly with cleaning agents that are also used for sterilizing preforms.

BRIEF DESCRIPTION OF THE DRAWINGS

A preferred embodiment of the blow molding machine according to the disclosure is shown in the drawing, in which.

DETAILED DESCRIPTION OF THE PREFERRED EMBODIMENT

Figure 1:
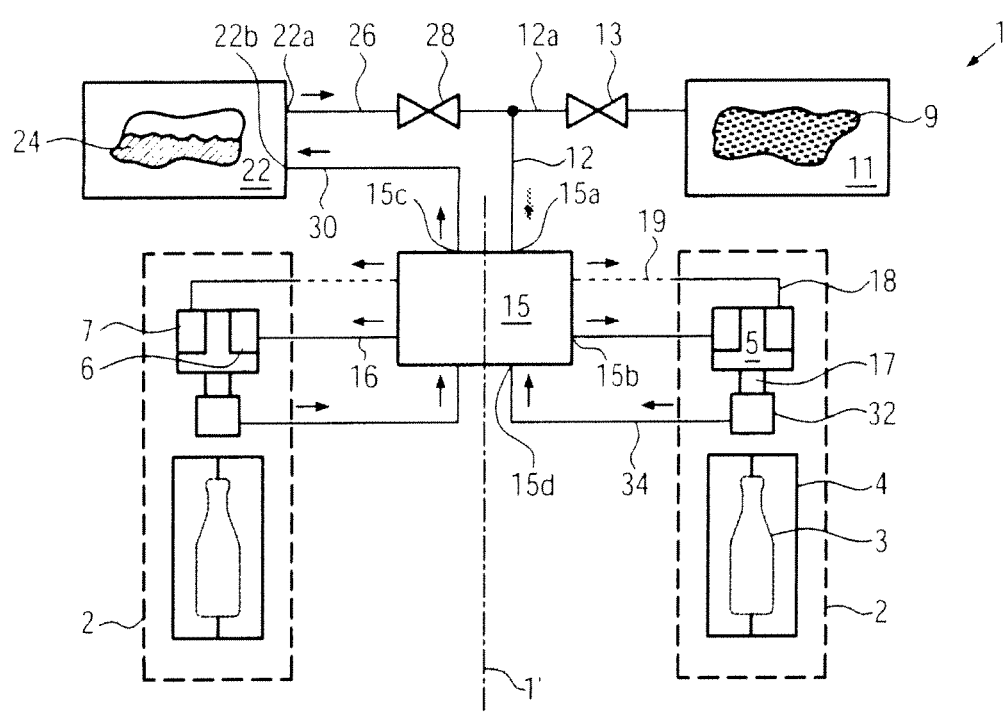
FIG. 1 is a schematic illustration of a blow molding machine according to the disclosure with CIP system.

As can be seen in FIG. 1, the blow molding machine 1 is configured in the embodiment in the known way as a rotary machine with a plurality of blow molding stations 2 arranged in symmetry around a rotational axis 1' and used for producing plastic bottles 3, wherein each blow molding station is equipped with a blow mold 4 and a valve block 5 with valves 6, 7 for introducing or discharging blowing air 9.

A compressor 11 for generating the blowing air 9 is connected through a blowing-air feed line 12 via a blowing-air shut-off valve 14 with the blowing-air inlet 15a of a media distributor 15 for distributing the blowing air 9 over the individual blow molding stations 2. The blowing-air exits 15b of the media distributor 15 are each connected through blowing-air feed channels 16 to a control valve 6 for introducing the blowing air 9 into a blowing nozzle 17 provided in the valve block 5. Moreover, at least one valve 7 and a blowing-air discharge channel 18 for discharging the blowing air 9 out of the blowing nozzle 17 and the blow mold, respectively, is provided on the valve block 5 and the blow molding station 2, respectively. FIG. 1 shows the blow molding machine 1 in a position with a valve block 5 lifted relative to the blow mold 4, so that the blowing nozzle 17 is accessible from underneath.

Furthermore, the blow molding machine 1 comprises a CIP cleaning system 20 with: a processing unit 22 for circulating and processing a cleaning agent 24; a CIP feed line 26 connecting an exit 22a of the processing unit 22 via a CIP main shut-off valve 28 to the blowing-air feed line 12 and the blowing-air inlet 15a, respectively, of the media distributor 15; a CIP return line 30 which connects a CIP outlet 15c of the media distributor 15 to an inlet 22b of the processing unit 22; and removable CIP sealing caps 32 with CIP collecting lines 34 for collecting and returning the cleaning agent 24 out of the blowing nozzles 17 into the CIP inlets 15d of the media distributor 15.

During the CIP operation the processing unit 22 pumps the cleaning agent 24 in the closed state of the blowing-air shut-off valve 13 and in the opened state of the CIP main shut-off valve 28 through the CIP feed line 26, the blowing-air feed line 12, the media distributor 15, the blowing-air feed channels 16, the valves 6, the blowing nozzles 17, the CIP sealing caps 32, the CIP collecting lines 34, the media distributor 15 and the CIP return line 30 in a circuit. The direction of flow of the cleaning agent 24 is symbolized in FIG. 1 by arrows. The blowing-air shut-off valve 13 only closes the section 12a of the blowing-air feed line 12 at the compressor side, so that neither blowing air 9 passes into the CIP circuit nor cleaning liquid 24 to the compressor 11.

During the CIP operation the cleaning agent 24 is simultaneously pumped through the blowing-air discharge channels 18 and the valves 7 into the blowing nozzles 17. Since the discharge channels 18 in the production process normally lead to the surrounding ambient air, these are connected in the CIP process via CIP connection lines 19 (plotted in broken line) to the CIP feed line 26 and to the media distributor 15, respectively, or to the blowing-air feed line 12.

Figure 2:
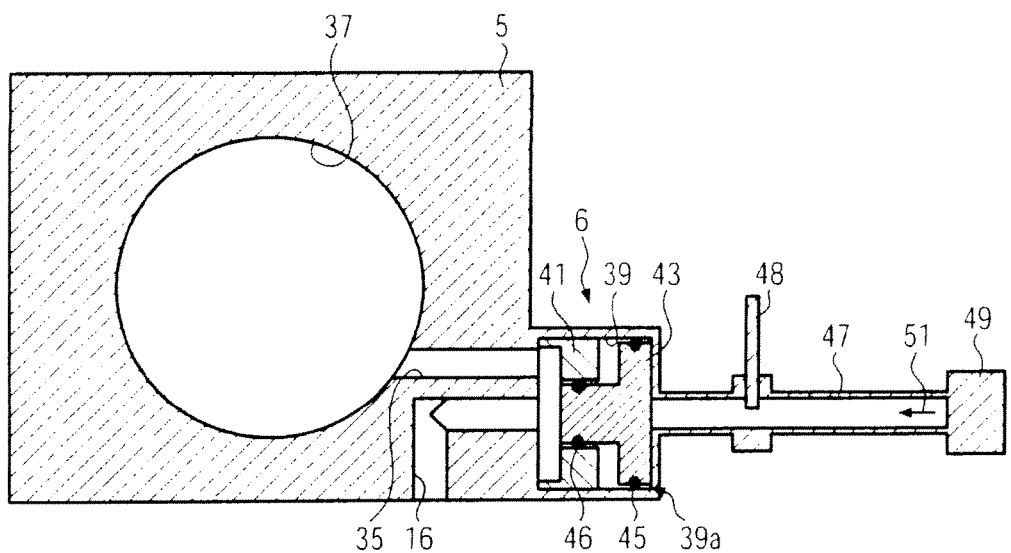
FIG. 2 is a schematic cross-section through a valve block with a pneumatically controlled valve for introducing blowing air.

FIG. 2 shows the valve block 5 in cross section, simplified with only one pneumatically operated opened valve 6 for introducing the blowing air 9 through the blowing-air feed channel 16 and a connection channel 35 into the blowing nozzle 17, for which an accommodating bore is provided in the valve block 5. The valve 6 comprises a cylinder 39 with a spacer sleeve 41, and a piston 43 with seals 45, 46 that seal the piston 43 relative to the cylinder 39 and the spacer sleeve 41, respectively.

The valve 6 is connected via a pneumatic control line 47, a CIP shut-off valve 48 (each of them not shown in FIG. 1 for the sake of clarity) and a conventional control or pilot valve 49 for opening/closing the valve 6 to a compressed air network that supplies compressed air 51 of e.g. 6 bar. In the production process the CIP shut-off valve 48 is opened. When the pilot valve 49 is opened, the compressed air 51 will press the piston 43 in the direction of the blowing-air feed channel 16 until it is closed. After the pilot valve 49 has been closed, the valve 6 can be opened again by the blowing air 9 which flows in via the blowing-air feed channel 16 and presses against the piston 43.

In the CIP process the CIP shut-off valve 48 is closed to prevent the cleaning agent 24 from passing into the pilot valve 49. Since the compressed air 51 is then not acting on the valve 6, the cleaning agent 24 that flows in through the blowing-air feed channel 16 presses the piston 43 to the right side, thereby opening the valve 6, and passes through the connection channel 35 into the blowing nozzle 17.

The seals 45, 46 prevent the cleaning agent 24 from penetrating into the portion 39a at the control side between piston 43 and cylinder 39—preferably entirely. However, it is also possible that the cleaning agent 24 that has penetrated into the portion 39a is blown for completion of the CIP process after opening of the CIP shut-off valve 48 by the compressed air 51 out of the cylinder 39 into the blowing nozzle 17. It would just as well be possible to evacuate the portion 39a via a vent channel (not shown) formed in the valve block 5, possibly supported by a heating of the portion 39a.

The seals 45, 46 consist of a material that is resistant to the cleaning agent 24, e.g. metal, EPDM rubber, perfluoro rubber (e.g. FFKM), or a suitable material composite. Preferably, Teflon rings may also be used. The seal 46 that seals relative to the spacer sleeve 41 is here not imperatively needed.

The CIP shut-off valve 48 may e.g. be an electromagnetically operated shut-off valve, e.g. a cock or a bolt.

The cleaning agent 24 is preferably a CIP sterilizing agent, as is e.g. used for sterilizing preforms. The cleaning agent 24 is preferably an acid or base, such as peracetic acid, hydrogen peroxide, or soap suds. The use of alcohols is possible.

The removable CIP sealing cap 32 tightly ends with the valve block 5 and the blowing nozzle 17, respectively, so that the circulating cleaning agent 24 can be collected completely, if possible, returned and processed. The CIP collecting line 34 may e.g. be a flexible line. It is decisive that for cleaning purposes the CIP sealing cap 32 can be mounted or removed, respectively, for the production process.

As a rule, blow molding machines operate with blowing air 9 of different pressure ranges, e.g. for pre-blowing, finish-blowing and inter-blowing, so that a plurality of valves 6 are then provided for introducing the blowing air 9. These are normally opened in alternating fashion. Likewise, a plurality of bleeder valves 7 for discharging the blowing air 9 may be provided, if necessary, the valves being normally opened together. For the sake of clarity FIG. 1 only shows one pressure system, e.g. that for the finishing blowing air. It goes without saying that additional valves 6, 7 and associated lines for additional low- or high-pressure systems may be provided in the blow molding machine 1 according to the disclosure.

Likewise, FIG. 2 only shows one valve 6 and the associated channels 16, 35 in a simplifying manner. Any desired number of valves 6, 7 with the associated channels 16, 35 may however be provided on the valve block 5. The design may also differ from the illustrated example. The relief valves 7 can be designed in conformity with the same operative principle as the introducing valves 6. However, it goes without saying that the position of the connection channel 35 and of the discharge channel 18 may differ from FIG. 2. For instance, the piston 43 could just as well close the connection channel 35. It is decisive that the valves 6, 7 and particularly the seals 45, 46 are not attacked by the cleaning agent 24 and can thus be integrated into the CIP system 20.

The CIP system 20 preferably operates in a circuit with processing of the cleaning agent 24. The cleaning agent can thus be used repeatedly with a constant sterilization action so as to save resources. After having flown through the blowing nozzle 17, however, the cleaning agent 24 could also be collected by the CIP sealing cap 32 and fed to a tank for disposal or separate processing.

The blow molding machine 1 according to the disclosure can be cleaned in the following way:

The blowing-air shut-off valve 13 and the CIP shut-off valves 48 are closed. After the CIP protection caps 32 have been mounted on the blowing nozzles 17a and the blowing-air discharge channels 18 have been connected to the outlets 15b of the media distributor 15 and the blowing-air feed line 12, respectively, the CIP main shut-off valve 28 is opened and the processing unit 22 is started. Said unit pumps cleaning agent 24 through the blowing-air feed channels 16 and the blowing-air discharge channels 18 up to the pistons 43 of the valves 6, 7. The pistons 43 are displaced by the pressure of the cleaning agent 24 and the valves 6, 7 are thereby opened, so that the cleaning agent 24 flows through the connection channels 35 into the blowing nozzles 17. The seals 45, 46 and the CIP shut-off valves 48 prevent the cleaning agent 24 from advancing up to the pilot valves 49. The cleaning agent 24 is collected by the CIP sealing caps 32 and returned by the media distributor 15 and the return line 30 into the processing unit 22. The unit regenerates the cleaning agent 24 and pumps it back into the CIP circuit. After a predetermined CIP flushing quantity and duration have been reached, the pumping function of the processing unit 22 is terminated and the CIP main shut-off valve 28 is closed again. Remaining cleaning agent 24 can now be discharged into the CIP sealing cap 32 and/or blown into it with blowing air 9 after the blowing-air shut-off valve 13 has been opened. In addition, after the CIP shut-off valve 48 has been opened, cleaning agent 24 passing over on the seals 45, 46 can be blown with the control type compressed air 51 out of the valve cylinder 39 into the blowing nozzle 17. The cleaning agent 24 that has been collected during evacuation of the feed lines 12, 16, 18 and of the media distributor 15 is also returned into the CIP circuit or disposed off.

The invention claimed is:

1. A blow molding machine for producing plastic bottles, comprising:
   a plurality of blow molding stations, the stations having assigned thereto valve blocks with valves and blowing nozzles for introducing or discharging blowing air;
   a cleaning-in-place system for cleaning the blow molding machine, comprising
      a processing unit for circulating and processing one or more cleaning-in-place agents within a cleaning-in-place circuit; and
      a cleaning-in-place feed line for the one or more cleaning-in-place agents, wherein the cleaning-in-place feed line being connected to a blowing-air feed line for the valves of the valve blocks;
   a media distributor for distributing the blowing air over the blow molding stations and for collecting the one or more cleaning-in-place agents;
   the valve blocks being included in the cleaning-in-place system; and
   a blowing-air shut-off valve provided in the blowing-air feed line of the valves of the valve blocks, wherein the blowing-air shut-off valve is configured to prevent, during a cleaning-in-place operation, at least one of
      the one or more cleaning-in-place agents from penetrating into a compressor for generating blowing air, and
      blowing air from exiting into the cleaning-in-place circuit, wherein the compressor being connected to the blowing-air feed line, and
   said blowing-air shut-off valve is disposed between the valve blocks and the compressor.

2. The blow molding machine according to claim 1, wherein the valves of the valve blocks are operated pneumatically.

3. The blow molding machine according to claim 1, and cleaning-in-place shut-off valves are provided on the valves of the valve blocks, for shutting off pneumatic control lines of the valves of the valve blocks.

4. The blow molding machine according to claim 1, wherein the valves of the valve blocks comprise seals that are resistant to the one or more cleaning-in-place agents.

5. The blow molding machine according to claim 1, wherein the cleaning-in-place system further comprises:
   cleaning-in-place sealing caps for collecting the one or more cleaning-in-place agents at the blow molding stations, wherein the cleaning-in-place sealing caps are at least one of mountable or removable, and the cleaning-in-place sealing caps being connected to a cleaning-in-place return line for returning the one or more cleaning-in-place agents into the processing unit.

6. The blow molding machine according to claim 5, wherein further, the media distributor is for introducing the collected one or more cleaning-in-place agents into the cleaning-in-place return line.

7. The blow molding machine according to claim 6, wherein a cleaning-in-place main shut-off valve is provided in the cleaning-in-place feed line.

8. The blow molding machine according to claim 4, wherein the one or more cleaning-in-place agents to which the seals are resistant include hydrogen peroxide.

* * * * *